(12) United States Patent
Zmiyiwsky et al.

(10) Patent No.: US 9,168,115 B2
(45) Date of Patent: Oct. 27, 2015

(54) BRISTLED TOOTHPICK ASSEMBLY AND METHOD OF USING THE SAME

(71) Applicant: ZEE ZEE CORPORATION, Mississauga (CA)

(72) Inventors: Zenovia Zmiyiwsky, Mississauga (CA); Vera Zmiyiwsky, Mississauga (CA); Robert G. Dickie, King City (CA)

(73) Assignee: Zee Zee Corporation, Mississauga, Ontario (CA)

( * ) Notice: Subject to any disclaimer, the term of this patent is extended or adjusted under 35 U.S.C. 154(b) by 0 days.

(21) Appl. No.: 14/063,288

(22) Filed: Oct. 25, 2013

(65) Prior Publication Data
US 2015/0114418 A1    Apr. 30, 2015

(51) Int. Cl.
| A61C 15/00 | (2006.01) |
| A61C 15/02 | (2006.01) |
| A61C 15/04 | (2006.01) |
| A46B 7/02  | (2006.01) |

(52) U.S. Cl.
CPC ............. *A61C 15/02* (2013.01); *A46B 7/023* (2013.01); *A61C 15/046* (2013.01); *A46B 2200/108* (2013.01)

(58) Field of Classification Search
CPC ........ A61C 15/00; A61C 15/02; A61C 15/04; A61C 15/041; A61C 15/042; A61C 15/046; A46B 9/02; A46B 9/025; A46B 9/028; A46B 7/023; A46B 2200/108
USPC ......... 132/321, 322, 323, 324, 328, 329, 123, 132/309, 317, 318, 320, 120, 141, 142; 433/142, 143, 149, 146, 147; 206/581, 206/823, 63.5, 368, 209, 209.1, 210, 361, 206/362, 362.1, 362.2, 362.3; 15/21.1, 15/22.1, 22.2, 106, 167.1, 167.2, 229.11; 401/29–33, 111, 167.2, 229.11; D4/105, 106, 116, 136; D28/65–68
See application file for complete search history.

(56) References Cited

U.S. PATENT DOCUMENTS

| 209,566    | A | * | 11/1878 | Holland ......................... 132/328 |
| 2,288,292  | A | * | 6/1942  | Maucher ......................... 401/31  |
| 2,519,502  | A | * | 8/1950  | Rem ............................... 401/31 |
| 3,511,249  | A | * | 5/1970  | Baitz ............................ 132/329 |
| 3,792,504  | A | * | 2/1974  | Smith ......................... 15/167.1  |
| 3,939,520  | A | * | 2/1976  | Axelsson .................... 15/167.1    |
| 4,449,933  | A | * | 5/1984  | Forni ............................ 433/141 |
| 4,517,701  | A | * | 5/1985  | Stanford, Jr. .................... 15/106 |
| 4,750,501  | A | * | 6/1988  | Ackermann et al. .......... 132/318       |
| 5,305,489  | A | * | 4/1994  | Lage ............................ 15/167.1 |

(Continued)

*Primary Examiner* — Vanitha Elgart
(74) *Attorney, Agent, or Firm* — Sand & Sebolt

(57) ABSTRACT

A toothpick assembly including a toothpick and a case within which the toothpick is detachably engaged. The toothpick includes a tapered tip which is generally triangular in cross-section having opposed sides connected by a generally flat end and an apex. A bristle array is provided on each side and the end and apex are free of bristles. The bristle array is configured as a sinuous or serpentine wave. Bristles in each array are smallest closest to an end of the tip and progressively increase in size as you move away therefrom. The toothpick is movable within the case's bore between a fully retracted, a partially extended and a fully extended position. A locking mechanism selectively locks the toothpick in any of these positions. When the toothpick is to be changed, the locking mechanism is disengaged and the toothpick is slid out of the bore and is replaced with another toothpick.

22 Claims, 10 Drawing Sheets

(56) References Cited

U.S. PATENT DOCUMENTS

| | | | |
|---|---|---|---|
| 5,435,033 A * | 7/1995 | Millner | 15/22.1 |
| 5,851,116 A * | 12/1998 | Margolis | 433/216 |
| 5,934,295 A * | 8/1999 | Gekhter et al. | 132/309 |
| 5,979,468 A * | 11/1999 | Blake, III | 132/318 |
| 6,085,761 A * | 7/2000 | Inaba | 132/329 |
| 6,253,404 B1 * | 7/2001 | Boland et al. | 15/22.1 |
| 6,468,080 B1 * | 10/2002 | Fischer et al. | 433/149 |
| 6,607,000 B2 * | 8/2003 | Marwah et al. | 132/321 |
| 6,669,475 B2 * | 12/2003 | Kandelman et al. | 433/89 |
| 6,957,467 B2 * | 10/2005 | Cabedo-Deslierres et al. | 15/106 |
| 8,011,057 B2 * | 9/2011 | Nejat | 15/167.1 |
| 2004/0094180 A1 * | 5/2004 | Hsu | 132/321 |
| 2005/0118553 A1 * | 6/2005 | Lagos Galvan | 433/141 |
| 2005/0257338 A1 * | 11/2005 | Brandli | 15/106 |
| 2006/0179593 A1 * | 8/2006 | Okamura | 15/167.1 |
| 2007/0017048 A1 * | 1/2007 | Ponzini | 15/167.1 |
| 2008/0251098 A1 | 10/2008 | Chen | |
| 2010/0269278 A1 * | 10/2010 | Huang | 15/167.1 |

* cited by examiner

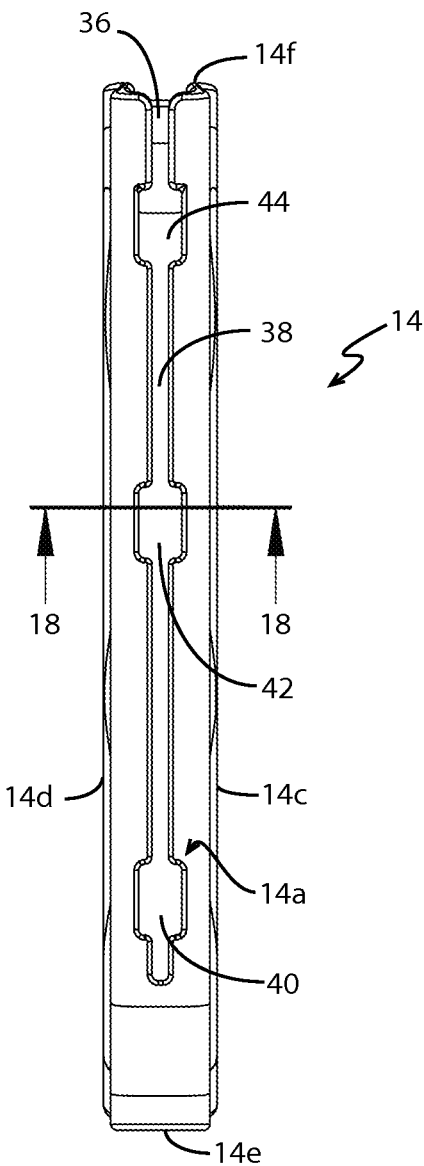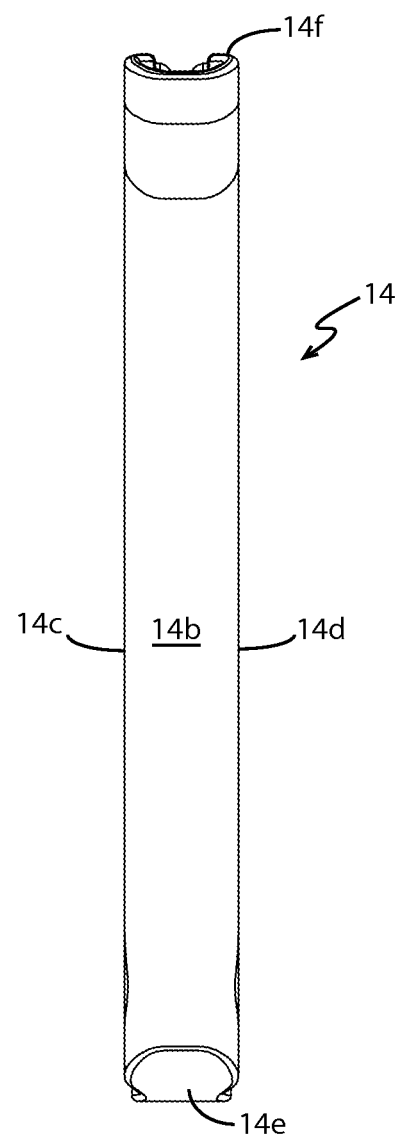
FIG. 16
FIG. 17

BRISTLED TOOTHPICK ASSEMBLY AND METHOD OF USING THE SAME

BACKGROUND OF THE INVENTION

1. Technical Field

This invention relates generally to dental products and their use. More particularly, this invention relates to a dental care product for removing food particles and plaque from interdental spaces. Specifically, the invention is directed to a toothpick having a tapered end which is triangular in cross-section and has bristles on two opposed sides. The bristles are configured in a serpentine wave on each side. An end face and an apex of the tapered end are free of bristles and one of these bristle-free regions is positioned adjacent the gingiva when the toothpick is used. The bristle arrays sweep particulate material from the sides of the teeth which bound the interdental space as the toothpick is moved back and forth. The bristle free region adjacent the gingiva helps ensure the gingiva is not unnecessarily irritated by this cleaning motion.

2. Background Information

Dental floss is used to remove residual food particles and plaque from the spaces between the teeth. Many people find floss difficult to use or they fail to use it in the most effective manner. Studies have therefore indicated that floss is not a particularly effective tool in preventing plaque build-up, gingivitis, and periodontitis. Toothpicks may be used to remove food particles from some spaces between the teeth but these devices typically do not clean the teeth effectively. Toothbrushes are also typically unable to penetrate far into and therefore clean the interproximal/interdental spaces adequately. The build-up of food particles and plaque in these spaces can lead to bad breath, infection and staining of the teeth. It is generally considered that if people have a dental care product which is both easy to use and effective, they will be more likely to include the use of that product in their daily dental routine.

In order to provide devices which clean interdental spaces, some have proposed adding bristles to toothpicks to make them more effective cleaning tools. For example, US Publication No. 2008/0251098 (Chen) discloses a toothpick which comprises a rod having bristles at one end. The tip of the rod is circular in cross-sectional shape and the bristles radiate outwardly from the circumferential exterior surface of the rod's tip. Bristles also extend outwardly and forwardly from the tip. One of the issues with this device is that because the bristles radiate outwardly in all directions, the bristles will come into contact with the gingiva when the toothpick is moved back and forth and up and down to remove food particles from the teeth and from the interdental space. The sandpapering effect of these bristles will irritate the gingival tissue. To address this problem, Chen has proposed coating the bristles with one of a variety of substances, such as toothpaste. The idea is that when these coated bristles contact the gingiva, the substance will help the bristles glide over the gingival tissue and thereby be less inclined to cut into and irritate that tissue. While this coating helps address the problems caused by raking the bristles over the gums, it does not completely eliminate this issue. Furthermore, the coating could also have the tendency to render the bristles slightly ineffective at cleaning food particles from the teeth because the coating acts as a lubricant which causes the bristles to easily glide across the food particles and tooth surfaces.

There is therefore a need in the art for an improved toothpick device for cleaning interproximal/interdental spaces.

SUMMARY

In one aspect, the invention may provide a toothpick assembly including a toothpick and a case within which the toothpick is detachably engaged. The toothpick includes a tapered tip which is generally triangular in cross-section having opposed sides connected by a generally flat end and an apex. A bristle array is provided on each side and the end and apex are free of bristles. The bristle array is configured as a sinuous or serpentine wave. Bristles in each array are smallest closest to an end of the tip and progressively increase in size as you move away therefrom. The toothpick is movable within the case's bore between a fully retracted, a partially extended and a fully extended position. A locking mechanism selectively locks the toothpick in any of these positions. When the toothpick is to be changed, the locking mechanism is disengaged and the toothpick is slid out of the bore and is replaced with another toothpick.

In another aspect, the invention may provide a method of cleaning an interdental space between two teeth extending outwardly from a patient's gingiva; said method comprising:

providing a toothpick having a tapered tip that is generally triangular in cross-section; wherein the tip has two opposed sides, an end surface extending between the sides and an apex opposite the end surface; a bristle array provided on each of the opposed sides of the tip; the end surface and apex being bristle free; and wherein each bristle array is disposed in a serpentine wave along the associated side; and in each bristle array, bristles progressively increase in length from proximate a free end of the tapered tip inwardly toward a second end of the toothpick;

inserting the tapered tip into the interdental space such that the bristle arrays encounter sides of the teeth and such that one or the other of the bristle-free end surface or apex is positioned adjacent the gingiva; and moving the tip back and forth within the interdental space to sweep the bristles across the sides of the teeth

BRIEF DESCRIPTION OF THE SEVERAL VIEWS OF THE DRAWINGS

A sample embodiment of the invention, illustrative of the best mode in which Applicant contemplates applying the principles, is set forth in the following description, is shown in the drawings and is particularly and distinctly pointed out and set forth in the appended claims.

FIG. 16 is a top view of the case of FIG. 14;

FIG. 17 is a bottom view of the case of FIG. 14; and

Similar numbers refer to similar parts throughout the drawings.

DETAILED DESCRIPTION

Referring to FIGS. 1-18, there is shown a bristled toothpick assembly in accordance with an aspect of the present invention, generally indicated at 10. Assembly 10 comprises a bristled toothpick 12 and a case 14. Toothpick 12 is shown in greater detail in FIGS. 8-13 and case 14 is shown in greater detail in FIGS. 14-18.

Figure 1:
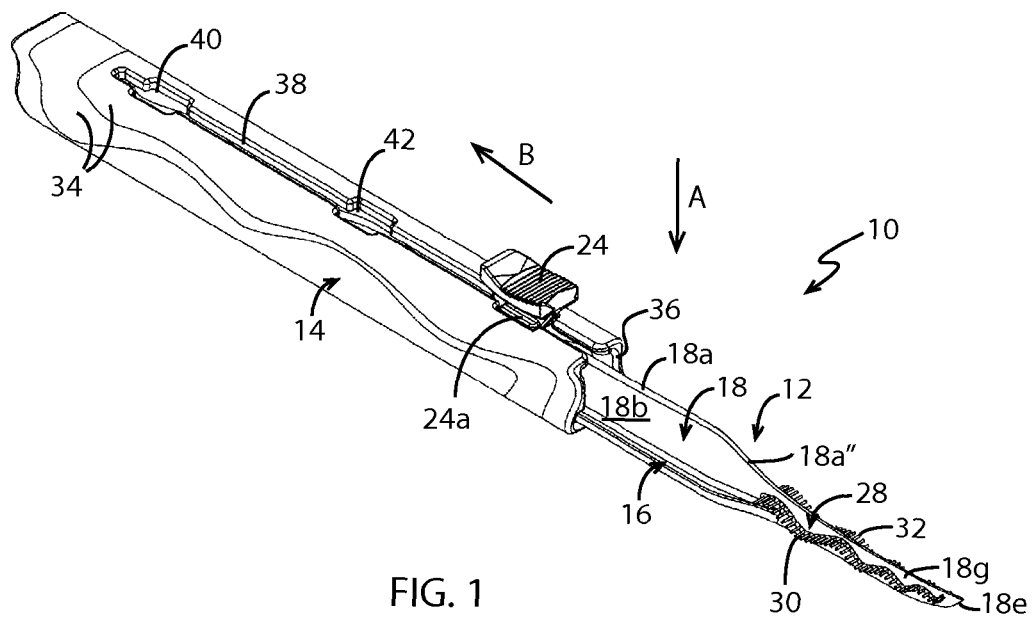
FIG. 1 is a perspective view of a bristled toothpick and case assembly in accordance with an aspect of the present invention; with the pick shown in a fully extended position where the pick is available for use.
Figure 2:
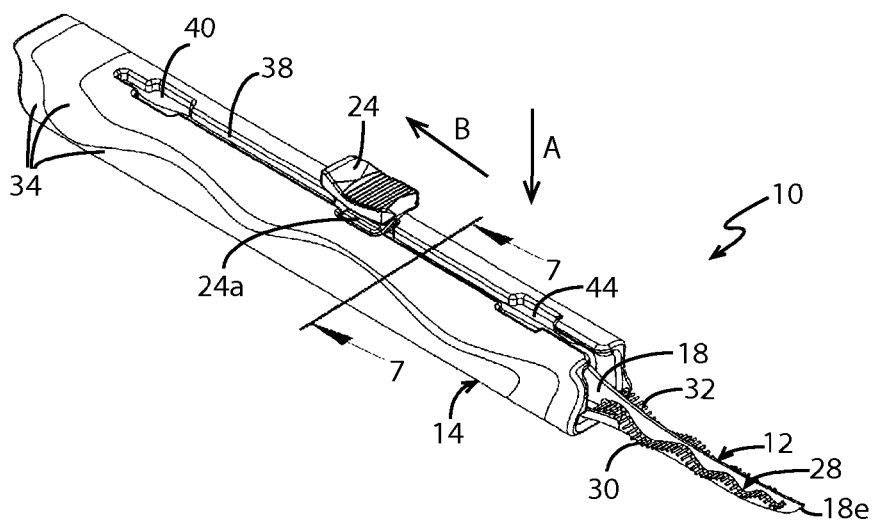
FIG. 2 is a perspective view of the assembly with the pick shown in a partially retracted position.
Figure 3:
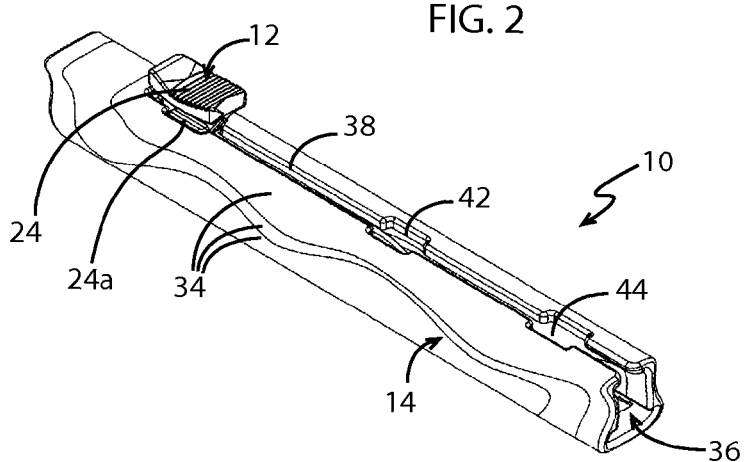
FIG. 3 is a perspective view of the assembly with the pick shown in a fully retracted position where the pick is in a storage position.
Figure 4:
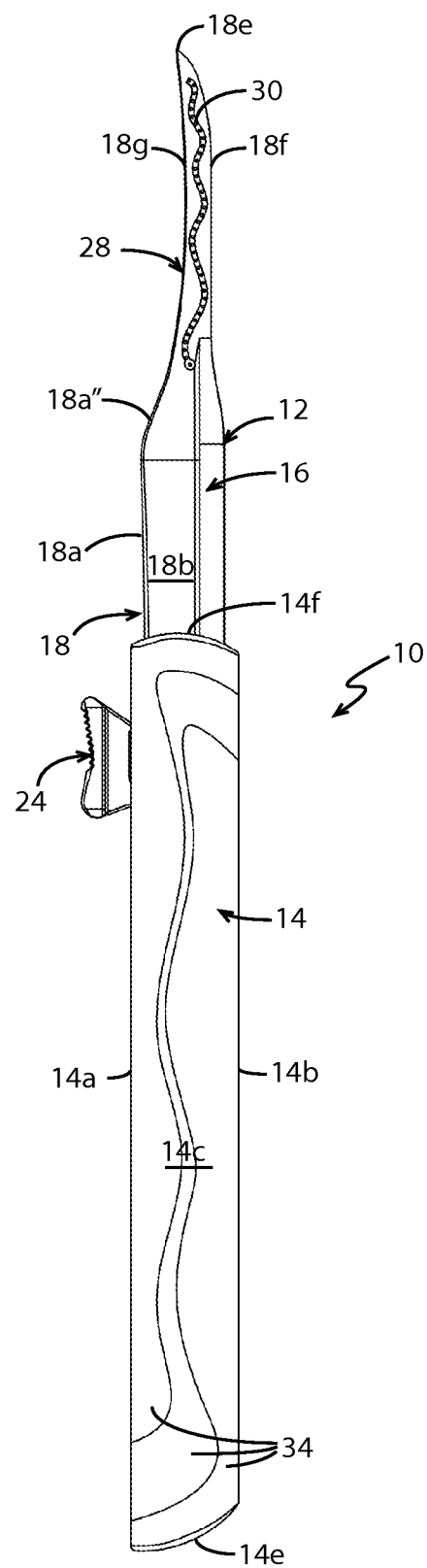
FIG. 4 is a right side view of the assembly shown in FIG. 1.
Figure 5:
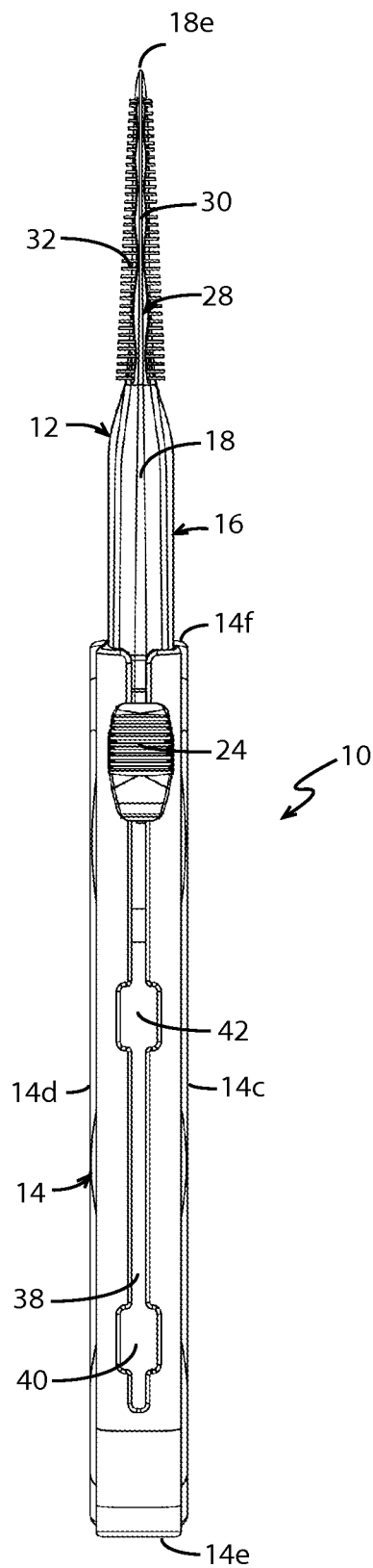
FIG. 5 is a top view of the assembly shown in FIG. 1.
Figure 6:
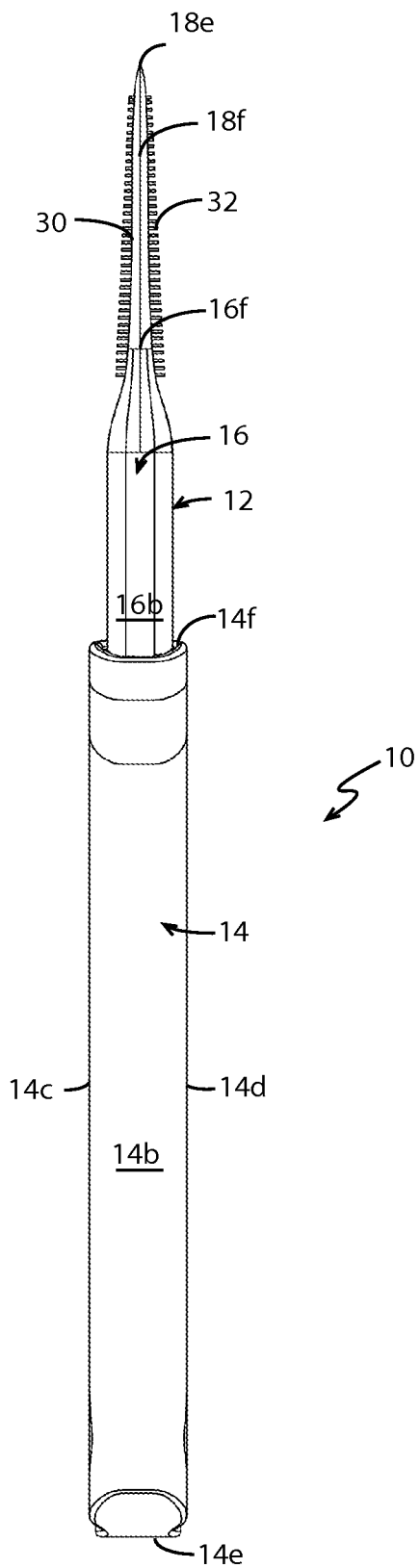
FIG. 6 is a bottom view of the assembly shown in FIG. 1.

Toothpick 12 is interlockingly engaged with case 14 and is movable therein between an extended position (FIG. 1), a partially extended position (FIG. 2); and a retracted position (FIG. 3). When in the fully or partially extended positions, toothpick 12 may be used to remove food particles and plaque from interdental spaces. Case 14 acts as a handle for toothpick 12 when the toothpick 12 is in either of the partially or fully extended positions and case 14 thereby makes it easier for a user to grip the toothpick and position it correctly within the mouth. When toothpick 12 is in the retracted position, substantially the entire toothpick 12 is disposed inside of the case 14 and toothpick 12 is no longer available for use. Case 14 effectively surrounds toothpick 12 and keeps it in a sanitary condition, ready for subsequent use.

Figure 9:
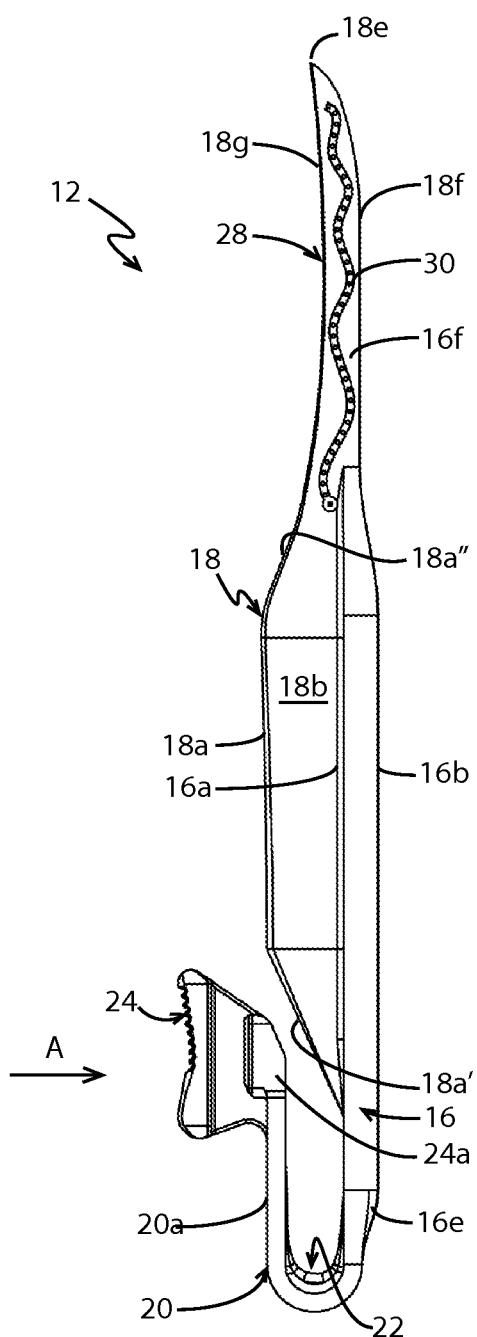
FIG. 9 is a right side view of the bristled toothpick of FIG. 8.
Figure 10:
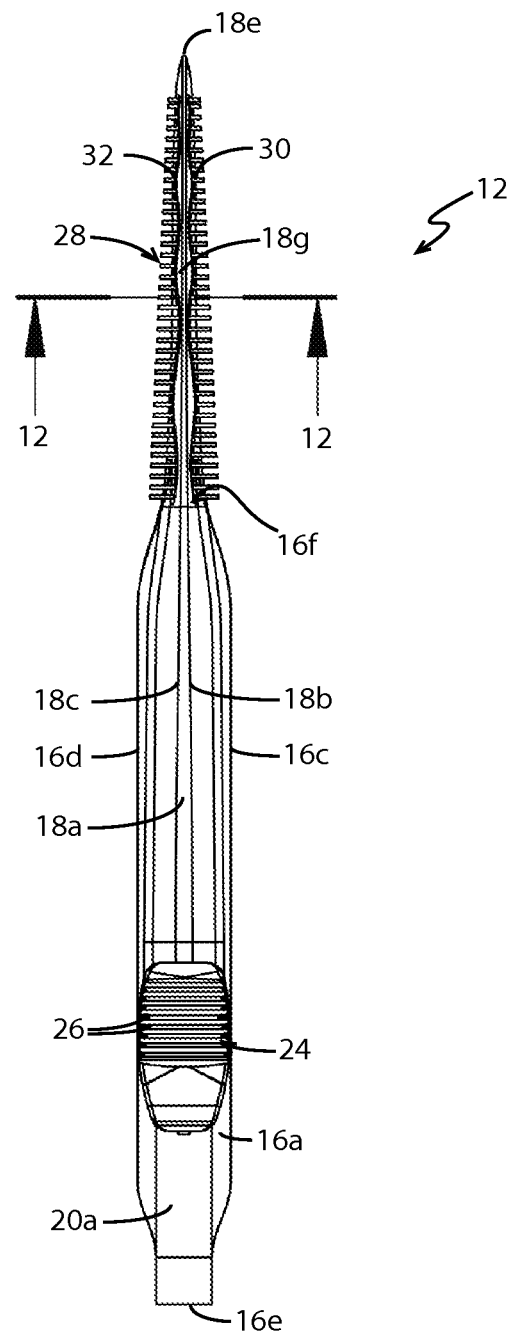
FIG. 10 is a top view of the bristled toothpick of FIG. 8.
Figure 11:
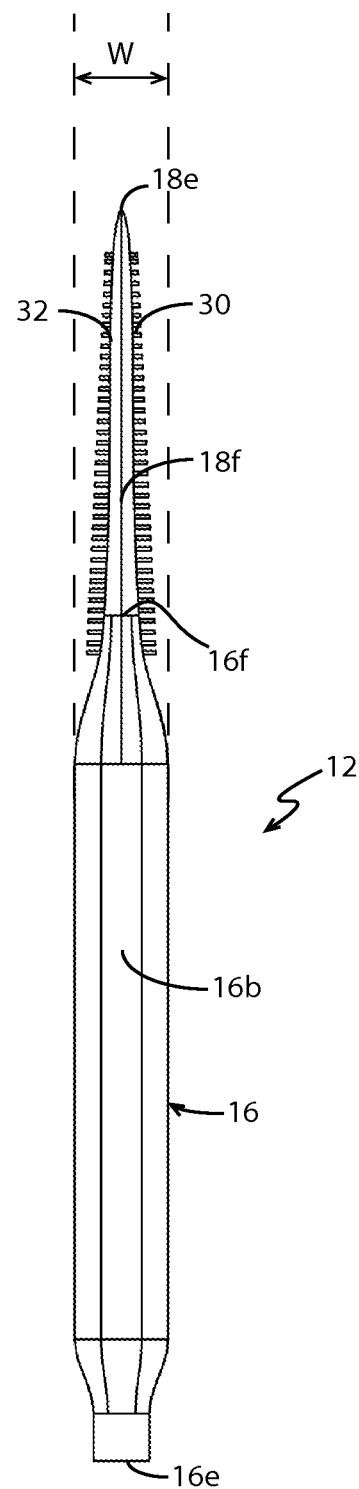
FIG. 11 is a bottom view of the bristled toothpick of FIG. 8.

Referring to FIGS. 8-13, toothpick 12 preferably is fabricated from a suitable plastic material and includes a base 16 and a flange 18. Base 16 and flange 18 may be molded as a single integral component or may be molded as separate components that are subsequently joined to each other, such as by heat welding. Base 16 is a generally rectangular member having a top surface 16a, a bottom surface 16b, a first side 16c, a second side 16d, a first end 16e, and a second end 16f. Top and bottom surfaces 16a, 16b are generally planar, although bottom surface 16b angles upwardly toward top surface 16a proximate second end 16f of base 16. Thus, base 16 tapers slightly in thickness (as measured between top and bottom surfaces 16, 16b) proximate second end 16f. Additionally, as best seen in FIGS. 10 and 11 base 16 tapers in width (as measured from first side 16c to second side 16d) proximate each of first end 16e and second end 16f. Thus, base 16 has a width "W" proximate its midpoint between first and second ends 16e, 16f, and has a width that is less than width "W" at each of the first and second ends 16e, 16f.

As best seen in FIG. 9, first end 16e is doubled-back upon itself to form a generally U-shaped member 20. A leg 20a of U-shaped member 20 is disposed substantially parallel to top surface 16a of base and is spaced a distance above that top surface 16a. A gap 22 is thus defined between leg 20a and top surface 16a. A button 24 is provided at the end of leg 20a and extends upwardly away from top surface 16a of base 16. The construction of first end 16e of base 16 is such that button 24 is able to be depressed downwardly toward top surface 16a and when released, the leg 20a will spring back to its original position relative to top surface 16a. Button 24 is thus a spring-activated or spring-mounted button 24, the purpose of which will be described later herein. Button 24 preferably is provided with knurling 26 or some other type of gripping or texturing finish on its uppermost surface so that it a person's fingertip will not easily slip off the same when they contact button 24 therewith. Base 16 further includes a shoulder region 24a disposed between leg 20a and button 24. Shoulder region 24a is smaller in width and length than the rest of button 24. The purpose of shoulder region 24a will be further described herein.

Flange 18 extends upwardly and outwardly from top surface 16a of base 16 and preferably is disposed generally at right angles to top surface 16a. Flange 18 has a top surface 18a, a first side 18b, a second side 18c, a first end 18d and a second end 18e. Top surface 18a includes a first section that is generally parallel to top surface 16a of base 16; and then a second section 18a' (FIG. 9) that slopes downwardly and rearwardly toward top surface 16a and first end 16e and a third section 18a'' that slopes downwardly and forwardly toward top surface 16a and second end 16f. Second section 18a' terminates in first end 18d of flange 18. Third section 18a'' is considerably longer than second section 18a' and angles more gently downwardly toward top surface 16a and never actually intersects the same. Instead, third section 18a'' forms the top surface of a first region 28 of flange 18 which projects outwardly and forwardly from second end 16f of base. Third section 18a'' terminates at second end 18e. A bottom surface 18f of flange 18 extends outwardly and forwardly from second end 16f of base 16 and terminates at second end 18e. First region 28 angles upwardly very slightly (see FIG. 9).

Figure 12:
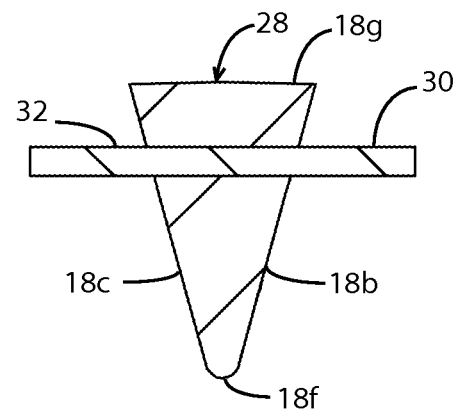
FIG. 12 is a cross-section of the bristled toothpick taken along line 12-12 of FIG. 10.

As can be seen from FIG. 12, first region 28 of flange 18 preferably is generally triangular in cross-section having sides 18b, 18c, an end 18g which extends between the opposed sides 18b, 18c, and an apex 18f. The specific orientation of first region 28 is immaterial in that end 18g may be disposed closer to top surface 18a and apex 18f closer to base 16 or end 18g may be disposed closer to base 16 and apex 18f disposed closer to top surface 18a. Either way, first region 28 is tapered when viewed from above (see FIG. 11) and is wider adjacent second end 16f of base 16 and narrower proximate second end 18e of flange 18.

In accordance with an aspect of the present invention, a pair of serpentine bristle arrays 30, 32 is provided on first region 28. Specifically each bristle array 30, 32 is fused to one of sides 18b, 18c of first region 28. Bristle arrays 30, 32 originate proximate top surface 16a of base 16 and extend to proximate second end 18e of flange 18 and are configured in a sinuous or serpentine wave along each side 18b, 18c The bristles in bristle arrays 30, 32 are shortest proximate second end 18e and become progressively longer as you move toward second end 16f of base 16. Consequently, the longest bristles in bristle arrays 30, 32 are disposed adjacent second end 16f.

In accordance with an aspect of the invention both surfaces 18g and apex 18f of first region 28 are free of bristles. In particular, they are smooth so as to be able to glide over the gingiva while the bristles arrays 30, 32 are sweeping particles from the interdental space as toothpick 12 is moved back and forth. Preferably, toothpick 12 is oriented to that flat end 18g will be disposed proximate the gumline during use.

When toothpick 12 is used, the narrower tip of the first region 28 of flange 18 and the very much smaller bristles at that tip 18e make it easier to insert toothpick 12 into the interdental spaces between teeth, even if those spaces are relatively narrow. The bristles on bristle arrays 30, 32 sweep against the side surfaces of the teeth which bound the interdental space, cleaning those side surfaces as the toothpick is moved into and out of the space. The serpentine profiles of bristle arrays 30, 32 vertically increase the surface area on the teeth that is cleaned by the simple back and forth motion of toothpick 12. (If the bristles were not disposed in a serpentine wave on toothpick 12, only a very narrow band of each tooth which bounds an interdental space would be cleaned by the bristles unless the toothpick was moved both back-and-forth and up-and-down in the interdental space. As it is, toothpick 12 is able to adequately clean the interdental space and sides of the teeth bounding the same using a simple back-and-forth motion. Additionally, because of the lack of bristles on surface 18g and apex 18f, there is little to no irritation of the gingiva.

FIG. 12 shows the first region of flange 18 in cross-section. As is evident from this figure, the first region 28 is generally triangular in cross-section and the bristle arrays 30-32 extend outwardly from sides 18b and 18c. The bristle arrays 30, 32 are sections of a single bristle assembly that is embedded in the material which is used to form the first region 28. During production, the bristle assembly is held in a mold and plastic is injected around the same, thereby embedding a central region of the bristle assembly within the material of toothpick 12.

Figure 13:
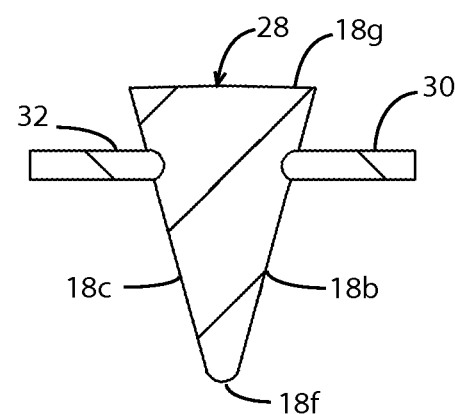
FIG. 13 is a cross-section of an alternative embodiment of the bristled toothpick taken along line 11-11 of FIG. 10.

FIG. 13 shows an alternative embodiment of the toothpick where there are two separate bristle arrays 30, 32 and each bristle array is separately fused into the material of the first region 28. So, in this instance, two bristle arrays are held within a mold and plastic is injected around the same to embed the inner ends of each bristle array within the material.

It will be understood that while first region 28 has been described herein as being preferably triangular in cross-section, a differently configured first region could be provided on the toothpick 12, Any differently configured first region would have at least one flat, bristle-free face thereon which extends between the sides on which the bristle arrays are provided, which bristle-free face would be positionable adjacent the gingiva when the toothpick assembly is used.

Figure 14:
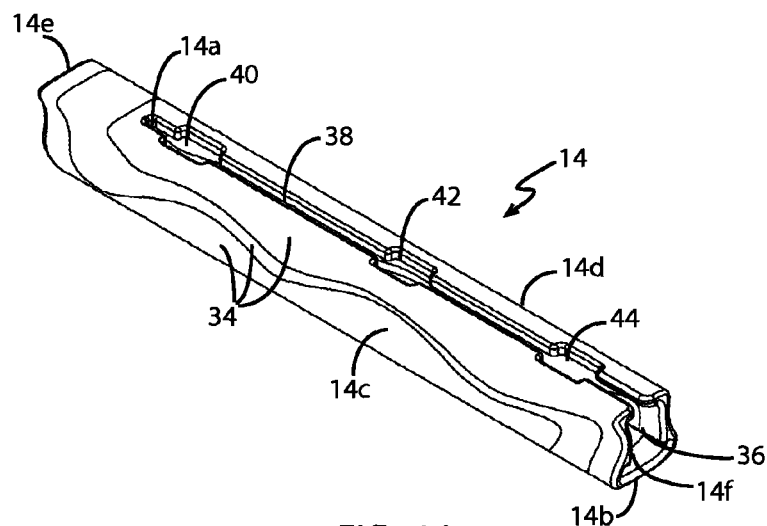
FIG. 14 is a perspective view of the case with the bristled toothpick removed therefrom.
Figure 15:
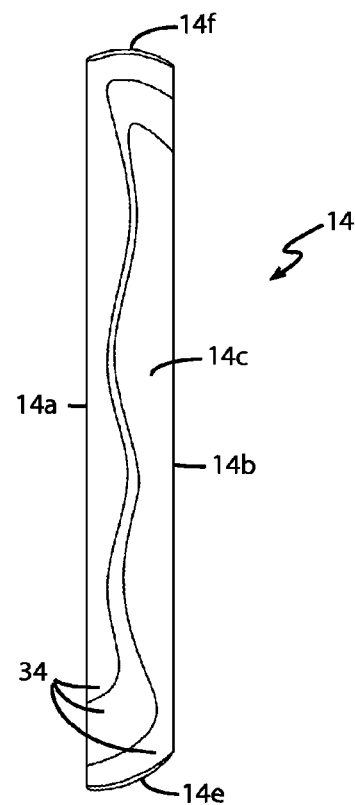
FIG. 15 is a right side view of the case of FIG. 14.

Referring to FIGS. 14-18 there is shown the case 14 which forms part of toothpick assembly 10 in accordance with an aspect of the invention. Case 14 is an elongate member that preferably is generally square in cross-sectional shape. Case 14 has a top surface 14a, a bottom surface 14b, a first side surface 14c, a second side surface 14d, a second end 14e, and a first end 14f. As best seen in FIG. 15, each of the first and second ends 14e is gently curved. Furthermore, the outside corners between top surface 14a and first and second sides 14c, 14d; and between bottom surface 14b and first and second sides 14c, 14d, are gently rounded. The curved ends 14e, 14f and corners help ensure that case is comfortable to hold and that case 14 presents no sharp edges which could hurt the user. Case 14 is ergonomically designed so that it easily fits within the palm of a user's hand and is able to be readily gripped between the thumb and fingers.

In accordance with an aspect of the invention, a double-injection elastomeric rubber coating is applied to case 14. This coating creates a waved-layering effect on the exterior surfaces of first and second sides 14c, 14d of case 14, making it easier for the user to grip case 14. These elastomeric layers are identified in the figures by the reference characters 34. The elastomer also helps ensure that case 14 is easily rinsed to keep it in sanitary condition. The wave-like design of the elastomeric rubber also makes the case 14 more aesthetically appealing.

Figure 18:
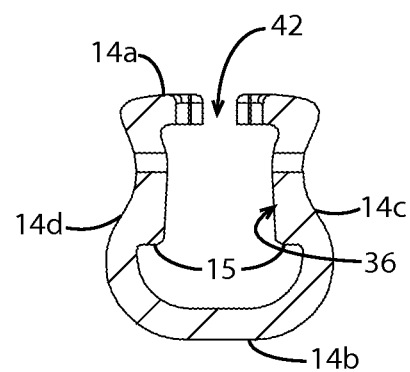
FIG. 18 is a cross-section of the case taken along line 18-18 of FIG. 16.

In accordance with another aspect of the invention, case 14 defines a bore 36 therein (FIGS. 14 and 18). Bore 36 originates in an opening in first end 14f and extends for a distance inwardly into case 14 and toward the second end 14e thereof. Preferably bore 36 extends all the way to the interior surface of second end 14e. There is no opening to bore 36 in second end 14e. Furthermore, top surface 14a defines a slot 38 therein. Slot 38 originates in first end 14f and extends for a distance toward second end 14e. Slot 38 is in communication with bore 36. At least one, but preferably three, holes 40, 42, 44 are defined in top surface 14a. Each hole 40, 42, 44 extends between an interior face of top surface 14a and an exterior face thereof. This can best be seen in FIG. 18. Holes 40, 42, 44 are also positioned to intersect slot 38. Holes 40, 42, 44 are also in communication with bore 36. Each hole 40, 42, 44 is dimensioned to be wider than slot 38 and, in particular, is shaped and sized so as to be slightly larger than shoulder region 24a of button 24. Button 24 itself is larger than shoulder region 24a and therefore cannot pass through any of holes 40, 42, 44. Shoulder region 24a is sized so as to be able to pass through any of holes 40, 42, 44, but is too large to pass through slot. (It will be understood that the number of holes defined in top surface 14a may be varied to be only one hole, two holes, three holes or even more than three holes without departing from the scope of the invention.)

Figure 7:
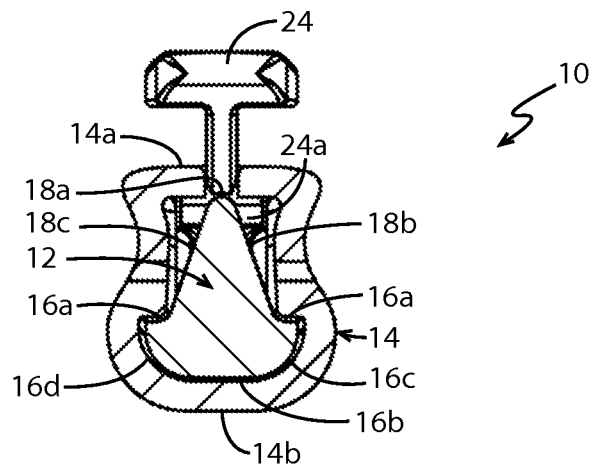
FIG. 7 is a cross-section taken along line 7-7 of FIG. 2.
Figure 8:
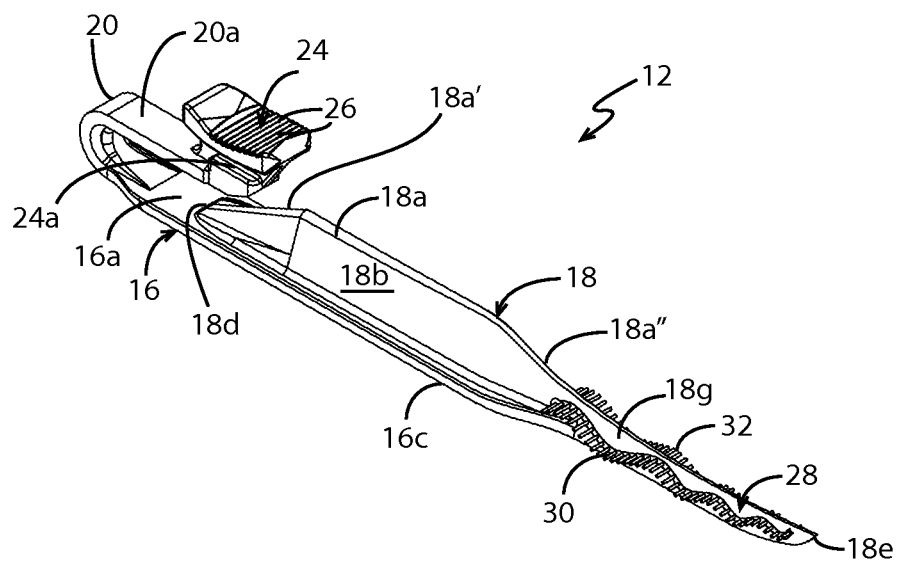
FIG. 8 is a perspective view of the bristled toothpick removed from the case.

FIG. 18 shows that the peripheral wall of case 14 which bounds and defines bore 36 is internally configured so as to form opposing shoulders 15. These shoulders 15 are shaped and positioned so as to engage top surface 16a of toothpick 12. When toothpick 12 is received within bore 36 (as is illustrated in FIG. 7), shoulders 15 act as a track along which top surface 16a slides as toothpick 12 is moved between the retracted and extended positions.

Toothpick 12 is engaged with case 14 by inserting first end 12e of toothpick 12 into the opening to bore 36 in second end 14e of case 14. When first end 12e of toothpick 12 is inserted therein, the U-shaped member 20 is caused to be slightly depressed downwardly in the direction of arrow "A" shown in FIG. 9. Bottom surface 16b of base 16 of toothpick 12 is slid inwardly along the interior of bottom surface 14b of case 14 and toward the second end 14e thereof. When shoulder region 24a of button 24 reaches hole 44, because of its complementary size and shape to hole 44, shoulder region 24a is capable of passing through hole 44 and tends to want to do this because of the spring-action of compressed member 20. Consequently, it is necessary to maintain downward pressure on button 24 while sliding toothpick 12 rearwardly toward second end 14e if it is not desired to lock toothpick 12 in the position dictated by shoulder region 24a engaging in hole 44. (Shoulder region 24a is complementary in size and shape to each hole 40, 42, 44.) Whenever shoulder region 24a pops upwardly through one of holes 40, 42 or 44, linear movement of toothpick 12 is arrested. Consequently, toothpick 12 is locked in position within case 14 whenever shoulder region 24a passes upwardly through one of holes 40, 42, or 44. The combination of the holes 40, 42, 44 and the complementary shoulder region 24a thus constitutes a locking mechanism for toothpick 12. It will be understood that other types of locking mechanism could be utilized instead of the one described and illustrated herein.

Toothpick 12 is movable between a use position (FIG. 1 or 2) and a storage position (FIG. 3). When toothpick 12 is in a fully extended position (FIG. 1), then shoulder region 24a passes upwardly in the opposite direction to arrow "A" and through hole 44. The entire first region 28 including the bristle arrays 30, 32 and a portion of flange 18 rearwardly of the first region 28 extends outwardly from the opening in case 14. In this fully extended position, toothpick 12 is able to be used to remove food particles from interdental spaces between a person's molars or any other teeth.

If it is desired to have less of flange 18 extend outwardly from case 14, then toothpick 12 is moved to the partially extended position (FIG. 2). This is accomplished by depressing button 24 in the direction of arrow "A" (FIG. 1) so that shoulder region 24a is pushed back into bore 36 of case 14. While initially depressing button 24 downwardly, button 24 is simultaneously moved toward second end 14e of case 14 in the direction of arrow "B". Once shoulder region 24a has cleared hole 44 it is no longer necessary to hold button 24 down as the interior of top surface 14a engages the upper portions of shoulder region 24a and keeps the same depressed downwardly. When button 24 reaches hole 42, shoulder region 24a will pass through the hole in the direction opposite to arrow "A" under spring pressure as the downward pressure on member 20 is released. Button 24 is thus locked in the position shown in FIG. 2 and in this position only the first region 28 of the flange 18 (with bristle arrays 30, 32) extends outwardly from first end 14f of case 14. In this position, toothpick 12 may be used to clean teeth, particularly near the front of the mouth. This partially extended position enables a user to use the toothpick assembly 10 discretely in public.

Figure 19:
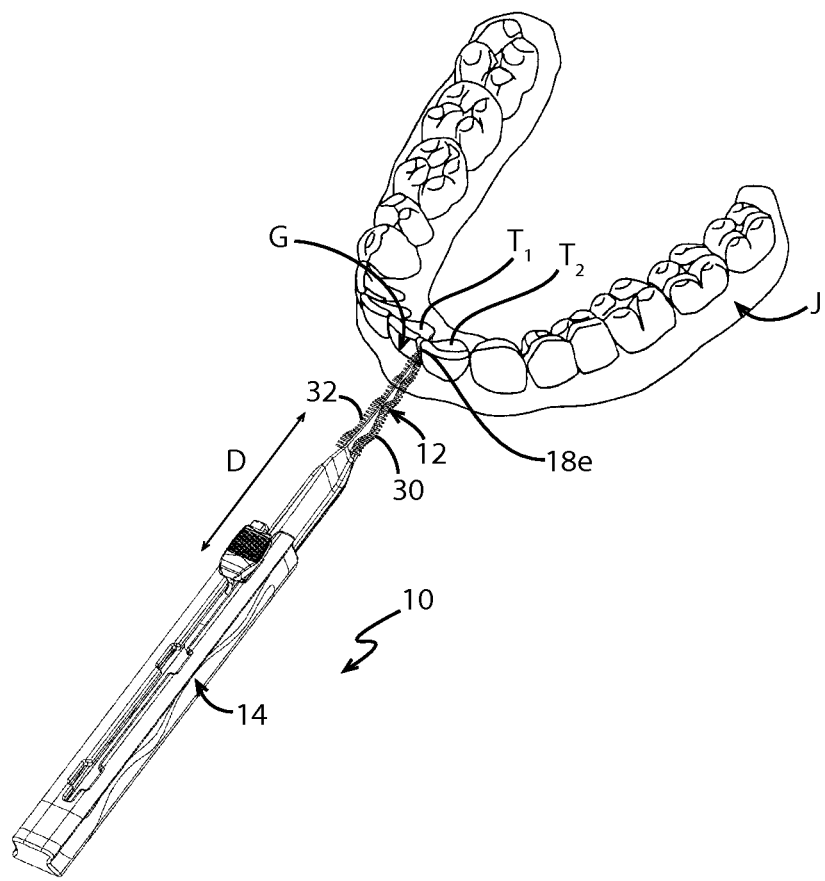
FIG. 19 is a perspective view of the lower jaw showing the bristled toothpick assembly being used to remove food particles and plaque from an interdental space between two teeth.

FIG. 19 shows bristled toothpick assembly 10 being used to clean and interdental space (not numbered) between a first tooth "T1" and a second tooth "T2" on a lower jaw "J" of a user. Toothpick 12 is moved in this instance into a fully extended position and the tip 18e of toothpick 12 is inserted into the interdental space. Using handle 14, toothpick 12 is moved back and forth (as indicated by arrow "D" so as to cause bristle arrays 30, 32 to remove particulate material (food particles and plaque) from the side surfaces of teeth T1, T2. It will be understood that bristled toothpick assembly 10 may be used in the orientation shown in FIG. 19 where bottom surface 18f (shown in FIG. 9) will contact the gingiva "G"; or bristled toothpick assembly 10 may be rotated through 180° to bring upper surface 18g into contact with gingiva "G". The assembly 10 may be used in a similar manner to clean interdental spaces between teeth of the user's upper jaw (not shown). As indicated previously, toothpick assembly 10 may be moved to a partially extended position for cleaning interdental spaces.

After use, bristled toothpick assembly 10 is preferably cleaned by running water over the same to flush food particles and plaque from bristle arrays 30, 32. Toothpick 12 preferably is subsequently moved into a fully retracted position so that assembly 10 may be stored. If toothpick is in either the fully extended or the partially extended position and it is desirable to store toothpick 12, then button 24 is depressed in the direction of arrow "A" (FIG. 1 or 2) and pressure is applied to simultaneously move button 24 rearwardly toward second end 14e of case 14 in the direction of arrow "B" (FIG. 2). Assuming toothpick 24 is in the partially extended position shown in FIG. 2, once shoulder region 24a has cleared hole 42, downward pressure on button 24 is no longer necessary. When button 24 reaches hole 40, the spring force in member 20 causes shoulder region 24a to pass through hole 40 and button 24 becomes locked in hole 40. In this position, substantially the entire toothpick 12 is fully retracted into bore 36 of case 14.

Case 14 is sufficiently small enough that it can be placed in a pocket or a purse and, because of its design, case 14 protects toothpick 12 from contamination and damage. Unlike previously known devices that utilize separate closures or covers which may be misplaced or may encourage and contribute to unhealthy bacterial growth, the present device protects the bristles and prevents them from being exposed to unsafe bacteria-rich environments.

If it is subsequently desired to move toothpick 12 into a position where it may be used, the user will depress button 24 in the direction of arrow "A" and then simultaneously move button 24 forwardly in the direction of arrow "C" (FIG. 3) to align shoulder 24a with either hole 42 or hole 44. Toothpick 12 may also be moved to the fully extended position to rinse the same so to remove any food particles and plaque trapped in bristle arrays 30, 32. If it is determined after a period of use that toothpick 12 has reached the end of its effective life, toothpick 12 is entirely removed from bore 36 and is disposed of. A new replacement toothpick (not shown) is inserted into bore 36 and is interlockingly engaged therewith as previously described. Case 14 is thus reusable for a substantial period of time, making the entire device more environmentally friendly than many other known interproximal dental devices. Toothpick assembly 10 may be sold as a kit which includes a case 14 and a plurality of substantially identical toothpicks 12 which are selectively engageable with case 14.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the invention are an example and the invention is not limited to the exact details shown or described.

The invention claimed is:

1. A toothpick assembly comprising;
   a toothpick comprising:
      a base with a first end and a second end;
      a first region extending outwardly from the second end of the base; wherein the first region is adapted to be insertable into a space between two teeth; said first region of the toothpick including a top, a bottom, a first side and a second side which extend between the top and bottom, and wherein the first and second sides terminate in a tip that is located remote from the second end of the base; and
   a plurality of bristles extend outwardly from a portion of each of the first and second sides of the first region; wherein the bristles progressively increase in length from proximate the tip of the first region to proximate the second end of the base; and wherein the bristles are arranged in a sinuous wave along each of the first and second sides of the first region; and wherein the bottom of the first region, which is adapted to be oriented adjacent the gingiva between the two teeth, is free of bristles.

2. The toothpick assembly as defined in claim 1, wherein the first region is generally triangular in cross-section; and the top and bottom extend between the first and second sides; and one of the top and bottom is generally flat and the other of the top and bottom forms an apex of the triangular shape.

3. The toothpick assembly as defined in claim 2, wherein each of the top and bottom is free of bristles and is adapted to be selectively disposed adjacent the gingiva.

4. The toothpick assembly as defined in claim 2, wherein a portion of the first region tapers in width from proximate the second end of the base toward the tip; and wherein this tapered portion of the first region includes the plurality of bristles thereon and the rest of the toothpick is free of bristles.

5. The toothpick assembly as defined in claim 4, wherein the plurality of bristles extending from each of the first and second sides are grouped into a bristle array, and the bristle array is sinuous along the length of the tapered region.

6. The toothpick assembly as defined in claim 5, wherein the plurality of bristles extending from each of the first and second sides is grouped into a single bristle array, and an inner region of the bristle array is embedded in a material from which the toothpick is molded and the inner region extends through the first region from the first side to the second side thereof.

7. The toothpick assembly as defined in claim 4, wherein the plurality of bristles extending from each of the first and second sides is grouped into two separate bristle arrays with a first one of the two bristle arrays extending outwardly from the first side and a second one of the two bristle arrays extending outwardly from the second side; and wherein an inner region of each of the bristles arrays is embedded in a material from which the toothpick is molded.

8. The toothpick assembly as defined in claim 1, further comprising a case having a bore defined therein; and wherein the toothpick is received within the bore and is interlockingly engaged with the case; and wherein the toothpick is movable within the bore between a first retracted, non-use position; and a second extended position where the toothpick is able to be used.

9. The toothpick assembly as defined in claim 8, wherein the case includes a top, a bottom, a first side and a second side extending between the top and bottom; a first end, and a second end; and
 the bore is defined in the case such that it originates in the first end of the case and extends for a distance inwardly toward the second end of the case; wherein the bore is accessible through an opening in the first end of the case; and wherein the toothpick is received through the opening into the bore; and when the toothpick is in the first position, substantially the entire toothpick is disposed within the bore; and when the toothpick is in the second position, a first part of the toothpick extends out of the opening and a second part of the toothpick is retained within the bore.

10. The toothpick assembly as defined in claim 9, further comprising a locking mechanism which secures the toothpick within the bore of the case at both of the first and second positions.

11. A toothpick assembly comprising;
 a toothpick comprising:
  a base with a first end and a second end;
  a first region extending outwardly from the second end of the base; wherein the first region is adapted to be insertable into a space between two teeth; said first region of the toothpick including a top, a bottom, a first side and a second side which extend between the top and bottom, and wherein the first and second sides terminate in a tip that is located remote from the second end of the base; and
  a plurality of bristles extend outwardly from a portion of each of the first and second sides of the first region; and wherein the bottom of the first region, which is adapted to be oriented adjacent the gingiva between the two teeth, is free of bristles;
 a case having a bore defined therein; and wherein the toothpick is received within the bore and is interlockingly engaged with the case; and wherein the toothpick is movable within the bore between a first retracted, non-use position; and a second extended position where the toothpick is able to be used; wherein the case includes a top, a bottom, a first side and a second side extending between the top and bottom; a first end, and a second end; and the bore is defined in the case such that the bore originates in the first end of the case and extends for a distance inwardly toward the second end of the case; wherein the bore is accessible through an opening in the first end of the case; and wherein the toothpick is received through the opening into the bore; and when the toothpick is in the first position, substantially the entire toothpick is disposed within the bore; and when the toothpick is in the second position, a first part of the toothpick extends out of the opening and a second part of the toothpick is retained within the bore; and
 a locking mechanism which secures the toothpick within the bore of the case at both of the first and second positions; and wherein the locking mechanism comprises:
  a slot defined in the top of the case, said slot originating at the first end of the case and extending toward the second end thereof; and wherein the slot is in communication with the bore;
  a first hole and a second hole defined in the top of the case intersecting the slot and spaced from each other; and said first and second holes are wider than the slot; and
  a spring-mounted button provided on the toothpick, said button having a shoulder region complementary to both of the first and second holes; wherein the button is disposed adjacent an exterior surface of the case and when the toothpick is in either of the first and second positions, the shoulder region of the button is seated within an associated one of the first and second holes; and when the toothpick is moved between the first and second positions, the shoulder region of the button is disposed inwardly of an interior surface of the case which defines the bore.

12. The toothpick assembly as defined in claim 11, wherein the first end of the base is turned back upon itself to form a U-shaped spring member; and
 the button is provided on the spring member.

13. The toothpick assembly as defined in claim 11, further comprising a third hole defined in the top of the case intersecting the slot and formed wider than the slot; said third hole being defined proximate the first end of the case, said first hole being defined proximate the second end of the case, and said second hole being disposed intermediate the first and third holes; and wherein the toothpick is selectively movable within the bore to align the shoulder region with one of the first, second or third holes; and when the shoulder region is aligned with the first hole, substantially the entire toothpick is retracted into the bore; when the shoulder region is aligned with the second hole only a bristled end of the toothpick extends outwardly from the bore; and when the shoulder region is aligned with the third hole, both the bristled end and a bristle-free region of the toothpick extend outwardly from the bore.

14. The toothpick assembly as defined in claim 13, wherein the toothpick is interlockingly engaged with the case when the shoulder region is seated within any of the first, second and third holes.

15. The toothpick assembly as defined in claim 8, further comprising an elastomeric material applied over an exterior surface of the case.

16. The toothpick assembly as defined in claim 8, wherein the toothpick is selectively disengageable from the case and is disposable.

17. The toothpick assembly as defined in claim 11, wherein the first region is generally triangular in cross-section; and the top and bottom extend between the first and second sides; and one of the top and bottom is generally flat and the other of the top and bottom forms an apex of the triangular shape.

18. The toothpick assembly as defined in claim 17, wherein each of the top and bottom is free of bristles and is adapted to be selectively disposed adjacent the gingiva.

19. The toothpick assembly as defined in claim 17, wherein a portion of the first region tapers in width from proximate the second end of the base toward the tip; and wherein this tapered portion includes the plurality of bristles thereon and the rest of the toothpick is free of bristles.

20. The toothpick assembly as defined in claim 11, wherein the bristles are arranged in a sinuous or serpentine wave along each of the first and second sides of the first region and progressively increase in length from the tip of the first region to proximate the second end of the base.

21. The toothpick assembly as defined in claim 11, further comprising an elastomeric material applied over an exterior surface of the case.

22. The toothpick assembly as defined in claim 11, wherein the toothpick is selectively disengageable from the case and is disposable.

* * * * *